United States Patent [19]

Rosentreter et al.

[11] Patent Number: 4,686,229
[45] Date of Patent: Aug. 11, 1987

[54] 1,4-DIHYDROPYRIDINES

[75] Inventors: Ulrich Rosentreter; Elisabeth Perzborn; Friedel Seuter, all of Wuppertal, Fed. Rep. of Germany

[73] Assignee: Bayer Aktiengesellschaft, Leverkusen, Fed. Rep. of Germany

[21] Appl. No.: 765,908

[22] Filed: Aug. 14, 1985

[30] Foreign Application Priority Data

Aug. 30, 1984 [DE] Fed. Rep. of Germany ....... 3431862

[51] Int. Cl.⁴ .................... C07D 401/14; A61K 31/44
[52] U.S. Cl. ..................................... 514/332; 514/333; 514/252; 546/256; 546/262; 546/263; 544/238
[58] Field of Search ..................... 546/256, 262, 263; 514/332, 333

[56] References Cited

U.S. PATENT DOCUMENTS 4,515,799  5/1985  Campbell et al. ................... 546/256
4,558,058 12/1985  Schönafinger et al. ............ 546/256

Primary Examiner—Jane T. Fan
Attorney, Agent, or Firm—Sprung, Horn, Kramer & Woods

[57] ABSTRACT 1,4-Dihydropyridines of the formula

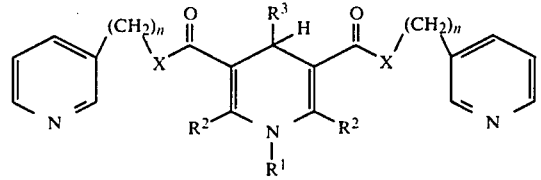

in which $R^1$ is hydrogen, or alkyl optionally substituted by halogen, nitro, cyano, alkoxy, carboxyl, alkoxycarbonyl or carboxamide, $R^2$ is hydrogen or alkyl, $R^3$ is hydrogen, alkyl, carboxyl, alkoxycarbonyl or aryl optionally substituted by hydroxyalkyl, carboxyl, sulphoxy, acloxyalkyl, or

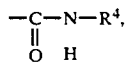

$R^4$ is alkyl, aryl, heteroaryl, aralkyl, heteroaralkyl,

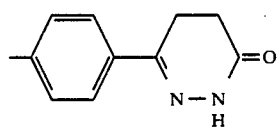

or

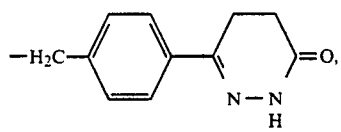

X is oxygen, sulphur or NH, and
n is 1 to 6, or physiologically acceptable salts thereof, which are active in combating thromboembolic and ischaemic disorders.

10 Claims, No Drawings

1,4-DIHYDROPYRIDINES

The present invention relates to new 1,4-dihydropyridines, processes for their preparation, and their use in medicaments, in particular in medicaments having an antithrombotic/anti-ischaemic activity.

The present invention relates to new 1,4-dihydropyridines of the general formula (I)

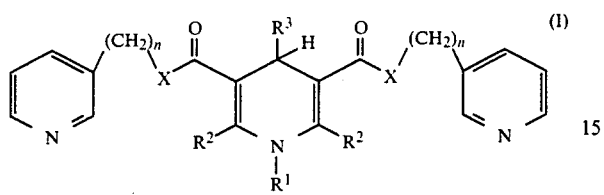

in which
R¹ represents hydrogen or alkyl (straight-chain or branched), optionally substituted by halogen, nitro, cyano, alkoxy, carboxyl, alkoxycarbonyl or carboxamide,
R² represents hydrogen or alkyl (straight-chain or branched),
R³ represents hydrogen, alkyl (straight-chain or branched), carboxyl, alkoxycarbonyl or aryl, optionally substituted by: hydroxyalkyl, carboxyl, sulphoxy, acyloxyalkyl, or the group

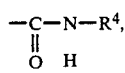

wherein R⁴ represents alkyl (straight-chain or branched), aryl, heteroaryl, aralkyl, heteroaralkyl or the groups

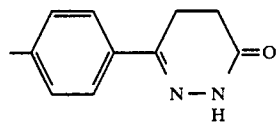

and

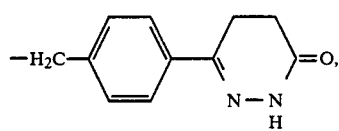

X denotes oxygen, sulphur or NH and
n assumes the values 1 to 6, and their physiologically acceptable salts, such as, for example: hydrochlorides, hydrogen sulphates, sulphates, hydrogen phosphates, formates, acetates, succinates, maleates, tartrates, lactates, citrates, fumarates or benzoates.

Preferred compounds of the formula (I) are those in which
R¹ represents hydrogen or alkyl (straight-chain or branched) having 1 to 5C atoms, optionally substituted by carboxyl or alkoxycarbonyl (having 1 to 4C atoms),
R² represents hydrogen or alkyl (straight-chain or branched) having 1 to 5C atoms,
R³ represents hydrogen or alkyl (straight-chain or branched) having 1 to 6C atoms, carboxyl, alkoxycarbonyl (having 1 to 4C atoms) or aryl (having 6 or 10C atoms), optionally substituted by hydroxyalkyl, acetoxyalkyl, benzoyloxyalkyl, each having up to 2C atoms, carboxyl, sulphoxy or the group

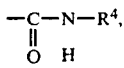

wherein
R⁴ represents alkyl (straight-chain or branched) having 1 to 4C atoms, phenyl, benzyl, pyridyl, pyridylmethyl, furfuryl or the groups

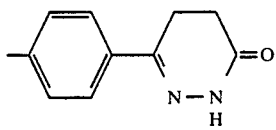

and

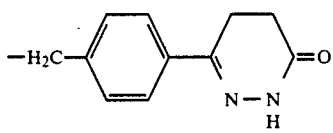

X denotes oxygen, sulphur or NH and
n assumes the values 1 to 6, and their physiologically acceptable salts.

Particularly preferred compounds of the formula (I) are those in which
R¹ represents hydrogen, alkyl (straight-chain or branched) having 1 to 4C atoms,
R² represents alkyl (straight-chain or branched) having 1 to 5C atoms,
R³ represents hydrogen, alkyl (straight-chain or branched) having 1 to 6C atoms, carboxyl, alkoxycarbonyl (having 1 to 4C atoms), or aryl (having 6 or 10C atoms), optionally substituted by hydroxymethyl, acetoxymethyl, carboxyl, sulphoxy or the group

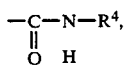

wherein
R⁴ represents alkyl (straight-chain or branched) having 1 to 4C atoms, phenyl, benzyl, pyridyl, pyridylmethyl, furfuryl or the groups

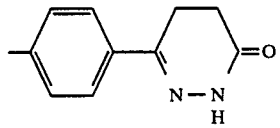

and

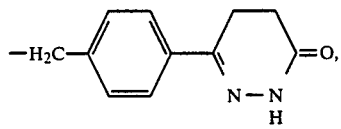

X represents oxygen or NH, and
n assumes the values 1 to 6, and their physiologically acceptable salts.

(A)

The compounds according to the invention, of the formula (I), wherein $R^3$ must not represent an aryl radical which is substituted by the group

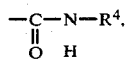

are obtainable by a method in which keto compounds of the general formula (II)

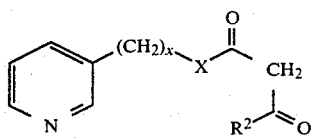

(II)

in which
$R^2$, X and n have the meaning given above,
are reacted with aldehydes of the general formula (III)

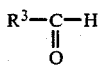

(III)

in which
$R^3$ has the meaning given above, but must not represent an aryl radical which is substituted by the group

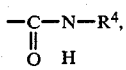

and amines of the general formula (IV)

 (IV)

in which
$R^1$ has the meaning given above,
in the presence of an inert organic solvent, and, if appropriate, the products are converted to their physiologically acceptable salts.

If 3-(pyrid-3-yl)-propyl acetoacetate, 4-formylbenzenesulphonic acid and ammonia are used as starting materials, the course of the reaction can be represented by the following equation:

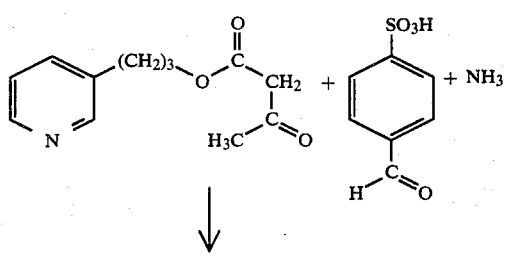

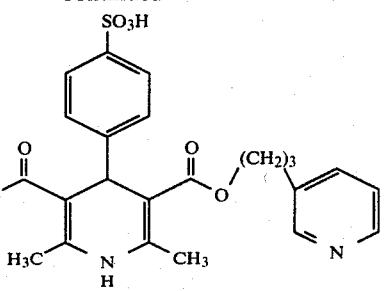

When the process according to the invention is carried out, the molar ratio of the keto compounds (II) to the aldehydes (III) is between 10:1 and 0.1:1, preferably between 2:1 and 0.5:1. The amine (IV) used is advantageously added in excess (about 1–3 molar amounts, relative to 1 mol of aldehyde).

Suitable solvents are water and all inert organic solvents. These preferably include alcohols, such as methanol, ethanol, propanol or isopropanol, ethers, such as diethyl ether, tetrahydrofuran or dioxane, glacial acetic acid, dimethylformamide, dimethyl sulphoxide, acetonitrile, pyridine and hexamethylphosphoric acid triamide.

The reaction temperatures can be varied within a relatively wide range. In general, the reaction is carried out at between 10° and 200° C., in particular between 20° and 150° C.

The reaction can be carried out under atmospheric pressure, or also under elevated pressure. In general, it is carried out under atmospheric pressure.

(B)

The compounds according to the invention, of the formula (I), wherein
$R^1$, $R^2$, X and n have the meaning given above, but
$R^3$ represents an aryl radical which is substituted by the group

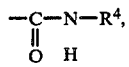

wherein
$R^4$ in turn has the meaning given above, can be prepared as follows:
Compounds of the general formula (I), in which
$R^1$, $R^2$, X and n have the meaning given above, but
$R^3$ represents

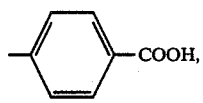

are first converted to activated carboxylic acid derivatives of the general formula (V)

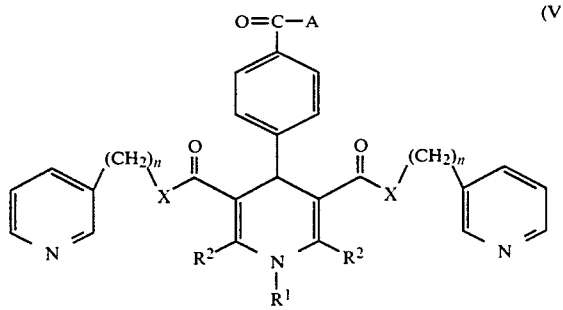

in which

R[1], R[2], X and n have the meaning given above and

A represents an electron-attracting radical, as conventionally used in peptide chemistry for the activation of carboxylic acids, and these are then reacted with amines of the general formula (VI)

$$H_2N-R^4 \qquad (VI)$$

in which

R[4] has the meaning given above, in the presence of bases, if appropriate in inert organic solvents.

If required, they are converted to their physiologically acceptable salts.

If di-3-(pyrid-3-yl)-propyl 4-(4-carboxyphenyl)-1,4-dihydro-2,6-dimethyl-pyridine-3,5-dicarboxylate and benzylamine are used as starting materials, the course of the reaction can be represented by the following equation:

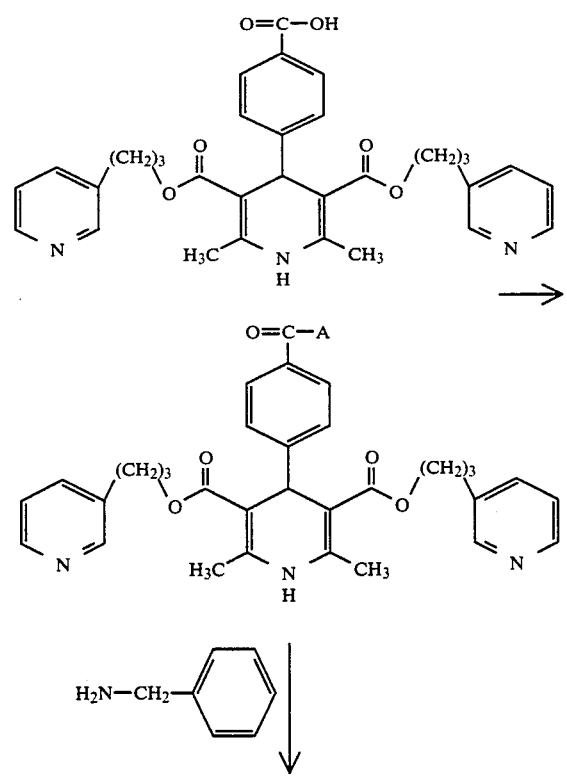

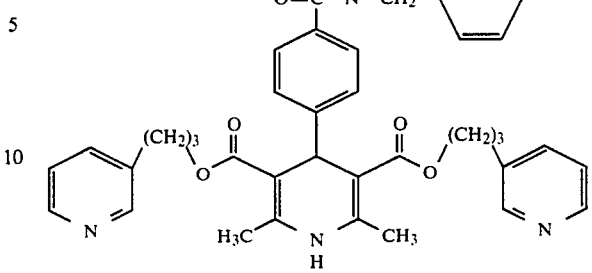

In carrying out the process according to the invention, the molar ratio of the amines (VI) to the active carboxylic acid derivatives (V) can be varied within a range from 10:1 to 0.1:1. Preferably, the process is carried out in the range between 2:1 and 0.5:1.

The reaction can be carried out in the presence of the customary bases, such as triethylamine, ethyldiisopropylamine, N-methylmorpholine, pyridine, 4-diethylaminopyridine or N,N-dimethylaniline.

Suitable solvents are the customary inert organic solvents. These preferably include chlorinated hydrocarbons, such as dichloromethane, trichloromethane or 1,2-dichloroethane, ethers, such as diethyl ether, tetrahydrofuran, dioxane or 1,2-dimethoxyethane, aromatic hydrocarbons, such as benzene or toluene, acetonitrile, nitromethane, dimethylformamide, hexamethylphosphoric acid triamide, pyridine, ethyl acetate and acetone.

The reaction temperatures can be, in general, between $-70°$ C. and $+60°$ C., preferably between $-60°$ C. and $+20°$ C.

The reaction can be carried out under atmospheric pressure, but also under elevated pressure. In general, it is carried out under atmospheric pressure.

Some of the keto compounds of the formula (II) are known, or can be prepared by methods which are in themselves known (cf. D. Borrmann, "Umsetzungen von Diketen mit Alkoholen, Phenolen und Mercaptanen" ("Reactions of Diketenes with Alcohols, Phenols and Mercaptans") in Houben-Weyl, Methoden der organischen Chemie (Methods of Organic Chemistry), volume VII/4, 230 et seq. (1968)).

Some of the aldehydes of the formula (III) are known, or can be prepared in the stated manner by known methods.

The amines of the general formulae (IV) and (VI) are known.

The compounds of the general formula (V) belong—depending on the meaning of the radical A—to the following substance classes, and can be prepared by known processes (cf. Houben-Weyl, Methoden der organischen Chemie (Methods of Organic Chemistry), volume XV/2, 1974): ethoxycarbonyl-methyl and diethoxycarbonyl-methyl esters, 2-oxopropyl esters, 2-diethylaminoethyl esters, bromomethyl esters, cyanomethyl esters, aminocarbonyl-methyl esters, propargyl esters, glycolates, ribosyl esters, phenyl esters, nitrophenyl esters, dinitrophenyl esters, dichloronitrophenyl esters, trichlorophenyl esters, pentachlorophenyl esters, pentafluorophenyl esters, 4-methylsulphonylphenyl esters, phenylazophenyl esters, 4-cyanophenyl esters, quinol-8-yl esters, 1-ethoxycarbonyl-2-ethoxy-1,2-dihydro-quinolyl esters, pyrid-3-yl esters, 2-hydroxyphenyl esters, 4-nitro-guaiacyl esters, 4-dimethylaminophenyl esters, 4-aminosulphonylphenyl esters, 4-(acetylaminosulphonyl)-phenyl esters, 4-propionylphenyl esters, vinyl esters, 1-methyl-2-acetylvinyl esters, 2,2-diphenylvinyl esters, 2-cyano-2-phenylvinyl esters, methoxy-methyl esters, tetrahydropyran-2-yl esters, 1-methoxy-vinyl esters, 1-ethoxy-vinyl esters, dimethylaminovinyl esters, N,N'-dicyclohexyllactim esters, N-ethyl-N'-(3-dimethylaminopropyl)-lactim esters, 2-hyroxypyridyl esters, O-acyl-N,N-dimethylhydroxylamines, O-acyl-N,N-diethyl-hydroxylamines, O-acyl-N,N-dibenzyl-hydroxylamines, N-hydroxy-piperidine esters, O-acyl-N-isopropylidene-hydroxylamines, N-hydroxy-pivaloamide esters, N-hydroxybenzamide esters, 1,2-dihydro-pyridon-1-yl esters, N-hydroxy-succinimide esters, N-hydroxy-glutaramide esters, N-hydroxy-phthalimide esters, N-hydroxy-quinoline acid imide esters, O-methyl-carbonic anhydrides, O-ethyl-carbonic anhydrides, O-isobutyl-carbonic anhydrides, O-benzyl-carbonic anhydrides, O-phenyl-carbonic anhydrides, 2-ethylbutyric anhydrides, 2,2-dimethyl-propionic anhydrides, diphenylacetic anhydrides, benzoic anhydrides, 4-methoxybenzoic anhydrides, O,O-dibenzylphosphoric anhydrides, O,O-di-(4-nitrobenzyl)-phosphoric anhydrides, methanesulphonic anhydrides, benzenesulphonic anhydrides, 4-methylbenzenesulphonic anhydrides, 4-nitrobenzenesulphonic anhydrides, 4-methoxybenzenesulphonic anhydrides, trifluoromethylsulphonic anhydrides, nonafluorobutylsulphonic anhydrides, phenylthio esters, 4-nitrophenylthio esters, phenylseleno esters, carboxylic acid azides, carboxylic acid imidazolides, carboxylic acid 1,2,4-triazolides, carboxylic acid 1,2,4-oxadiazolin-5-ones, acyl chlorides, acyl bromides, acyl iodides and acyl cyanides.

The above preparation processes are merely stated by way of illustration, and the preparation of the compound (I) is not restricted to this process, but any modification of the processes can be used in the customary manner for the preparation of the compounds (I) according to the invention.

The present invention furthermore relates to the use of the substances according to the invention, of the formula (I), as inhibitors/stimulants of enzymatic reactions in connection with arachidonic acid metabolism. Substances of this type are suitable for the prevention and treatment of disorders of the respiratory tract, such as emphysema, shock lung, pulmonary hypertension, oedema, thrombosis and thromboembolism, ischaemia (disturbances of peripheral, coronary and cerebral blood flow), cardiac and cerebral infarcts, cardiac arrhythmias, angina pectoris, hypertension and arteriosclerosis. The substances according to the invention are preferential inhibitors of thromboxane synthesis and at the same time stimulate the synthesis of prostacyclin.

The new active compounds can be converted in a known manner into the customary formulations (such as, for example, tablets, capsules, dragees, pills, granules, creams, suppositories, emulsions, suspensions and infusion and injection solutions) using inert non-toxic, pharmaceutically suitable excipients or solvents.

Particularly suitable are formulations which contain about 0.1 to 10% by weight of active compound, preferably aqueous solutions. Aqueous solutions with a pH value between 6 and 8 are particularly preferred.

The formulations are prepared by the customary methods, for example by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol) and glycols (for example propylene glycol and polyethylene glycol), solid excipients, such as natural rock powders (for example kaolins, aluminas, talc and chalk), synthetic rock powders (for example highly disperse silica and silicates) and sugars (for example sucrose, lactose and glucose), emulsifiers (for example polyoxyethylene fatty acid esters, polyoxyethylene fatty alcohol ethers, alkylsulphonates and arylsulphonates), dispersing agents (for example lignin, suphite waste liquors, methylcellulose, starch and polyvinylpyrrolidone) and lubricants (for example magnesium stearate, talc, stearic acid and sodium lauryl-sulphate).

Administration is effected locally, orally or parenterally, as required, in the customary manner.

Dosage is effected in general in a range from 0.05 to 100 mg/kg of body weight, in particular from 0.1 to 50 mg/kg of body weight.

In contrast to indometacin, which completely inhibits the synthesis of prostaglandin from arachidonic acid, the active compounds to be used according to the invention intervene much more specifically in the metabolism of the enzymes which are critical for the formation of prostacyclin ($PGI_2$) and of thromboxane, so that not only is the harmful, vasoconstricting and arrhythmia-increasing effect of the thromboxane reduced, but the vasodilating influence of the $PGI_2$ is increased by stimulation of its formation.

The biological action of the compound prepared according to the invention was demonstrated by the following experiments:

I.

$^3$H-arachidonic acid metabolism

The arachidonic acid metabolism in human platelets was investigated with the aid of tritium-labelled arachidonic acid. The platelets metabolized the arachidonic acid via the cyclooxygenase route to $TXA_2$ and HHT, and via the lipogenase route to 12-HETE, and these can be separated by thin-layer chromatography (cf. Bailey, J. M. et al., Prostaglandins 13, 479–492, 1977). Inhibitors of the individual enzymatic reactions modify the chromatographic distribution pattern in a characteristic manner.

Washed human platelets from healthy donors who had not taken any medicament for 14 days were incubated with test substance for 2 minutes at 37° C. and then incubated with $^3$H-arachidonic acid for a further 10 minutes at 37° C. The suspension was acidified, and extracted with ethyl acetate. The ethyl acetate was evaporated off under a nitrogen atmosphere, and the residue was taken up in methanol/trichloromethane (1:1) and the solution applied to TLC plastic films. Separation was carried out using, as the mobile phase, a trichloromethane/methanol/glacial acetic acid/water mixture (80:8:1:0.8). The distribution of the radioactivity was determined by means of a radioscanner.

II.

Prostacyclin stimulation

The 1,4-dihydropyridines to be used according to the invention also stimulate the synthesis of $PGI_2$. In contrast to thromboxane, which has a vasoconstricting action and initiates platelet aggregation, $PGI^2$ has a vasodilating action and inhibits platelet aggregation.

Stimulation in whole blood

The formation of $PGI_2$ can be induced in whole blood by collagen. The endoperoxides formed in platelets are probably converted into $PGI_2$ by leucocyte lipoxygenase. The stable end product of the $PGI_2$ conversion, 6-keto-$PGF_1\alpha$, is determined radioimmunologically.

III.

Platelets aggregation

Platelets and their adhesion—and ability to aggregate—are an important pathogenetic factor in the production of thromboses, particularly in the arterial branch of the vascular system. Surprisingly, the compounds according to the invention were effective in this test too, which, in conjunction with the other properties, makes the substance appear particularly advantageous.

For the in vitro tests, blood from healthy test subjects of both sexes was used. As an anticoagulant, one part of 3.8% strength aqueous sodium citrate solution was mixed with 9 parts of blood. By means of centrifuging, platelet-rich citrated plasma (PRP) (cf. Jürgens/Beller "Klinische Methoden der Blutgerinnungsanalyse" ("Clinical Methods of Blood Coagulation Analysis"); Thieme Verlag, Stuttgart 1959) is obtained from this blood.

For these investigations, 0.8 ml of PRP and 0.1 ml of the active compound solution were preincubated at 37° C. in a waterbath. Thereafter, the platelet aggregation was determined by the turbidometric method (cf. Born, B. V. R., J. Physiol. (London), 162, 67 (1962)) in an aggregometer at 37° C. (cf. Therapeutische Berichte 47, 80–86 (1975)). For this purpose, 0.1 ml of collagen, an aggregation-initiating agent, was added to the preincubated sample.

The change in the optical density in the sample of PRP was recorded during a period of 6 minutes, and the deflection was determined after 6 minutes. From this, the percentage inhibition compared with the control is calculated. The range of the minimum effective concentration is stated as the limiting concentration.

TABLE 1

| | Inhibition of the $TXA_2$ synthesis |
|---|---|
| Example No. | Limiting concentration for inhibition (mg/l) |
| 1 | 0.3–0.1 |
| 2 | 1–0.3 |
| 4 | 1–0.3 |
| 5 | 3–1 |
| 6 | 10–3 |
| 7 | 10–3 |
| 8 | 0.1–0.003 |
| 9 | 0.3–0.1 |
| 10 | 1–0.3 |
| 11 | 1–0.3 |

TABLE 2

| | Prostacyclin stimulation | |
|---|---|---|
| Example No. | Concentration (mg/l) | Stimulation (%) |
| 1 | 10–3 | 158 |
| 4 | 0.3–0.1 | ~50 |
| 5 | 0.3–0.1 | 100 |
| 9 | 1–0.1 | |
| 10 | 0.1–0.03 | ~50 |
| 11 | 0.1–0.03 | ~100 |

TABLE 3

| | Inhibition of platelet aggregation |
|---|---|
| Example No. | Limiting concentration for inhibition (mg/l) |
| 8 | 3–1 |

PREPARATION EXAMPLES

Example 1

Di-3-(pyrid-3-yl)-propyl 1,4-dihydro-4-(4-hydroxymethylphenyl)-2,6-dimethyl-pyridine-3,5-dicarboxylate

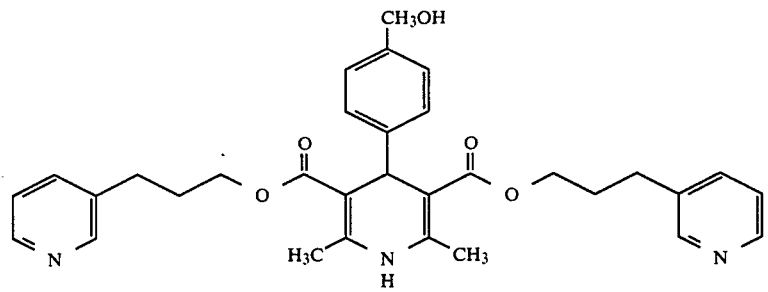

(a)

4-Hydroxymethylbenzaldehyde 200 g (1.44 mols) of terephthalic dialdehyde are suspended in 2,000 ml of methanol, and 23.5 g (0.62 mol) of sodium borohydride are added, while cooling with ice. After the mixture has been heated to room temperature, it is evaporated down under reduced pressure to a quarter of its volume, and extracted 3 times with dichloromethane. After the solution has been dried with sodium sulphate and the dichloromethane stripped off, 4-hydroxymethylbenzyl alcohol crystallized from ether. After the filtrate had been evaporated down, 61.7 g of crystalline product were obtained.

Yield: 61.7 g (34.5% of theory).

Melting point: 48° C.

(b)

Di-3-(pyrid-3-yl)-propyl 1,4-dihydro-4-(4-hydroxymethylphenyl)-2,6-dimethyl-pyridine-3,5-dicarboxylate 5 g of 3-(pyrid-3-yl)-propyl acetoacetate, together with 0.85 ml of 25% strength aqueous ammonia solution and 1.5 g of 4-hydroxymethylbenzaldehyde, in 20 ml of isopropanol are heated under reflux for 48 hours. After the reaction solution has been evaporated down, the product crystallizes from ether, and is recrystallized from ethyl acetate.

Yield: 0.7 g (12% of theory).
Melting point: 95° to 100° C.

Example 2

Di-3-(pyrid-3-yl)-propyl 4-(4-acetoxymethylphenyl)-1,4-dihydro-2,6-dimethyl-pyridine-3,5-dicarboxylate Melting point: 32° C.

(b)

Di-3-(pyrid-3-yl)-propyl 4-(4-acetoxymethylphenyl)-1,4-dihydro-2,6-dimethyl-pyridine-3,5-carboxylate 5 g of 3-(pyrid-3-yl)-propyl acetoacetate, together with 0.85 ml of 25% strength aqueous ammonia solution and 2.01 g of 4-acetoxymethylbenzaldehyde, in 20 ml of isopropanol are heated under reflux for 24 hours. The reaction solution is evaporated down and the residue is chromatographed over silica gel using a mixture of dichloromethane and methanol in a ratio of 95:5 as the eluting agent. A fraction which, when evaporated down, gives the product in the form of a solid is obtained in this manner.

Yield: 1.3 g (20% of theory).
Melting point: 89° to 94° C.

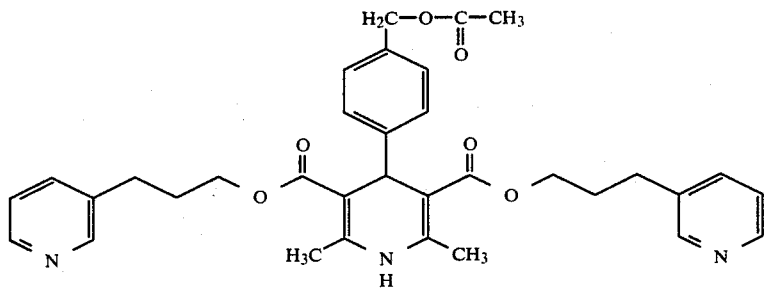

(a)

4-Acetoxymethylbenzaldehyde 54.2 g of 4-hydroxymethylbenzaldehyde, together with 40 g of triethylamine, are dissolved in 350 ml of dichloromethane. After the dropwise addition of 31.2 g of acetyl chloride at 0° to 5° C., the reaction mixture is allowed to stand overnight at room temperature. Thereafter, the precipitated triethylammonium chloride is filtered off under suction, and the filtrate is extracted 3 times with saturated bicarbonate solution. After it has been dried with sodium sulphate, the residue is distilled in a high vacuum. 47.9 g of a colorless solid are obtained in this manner.

Yield: 47.9 g (85% of theory).

Example 3

Di-3-(pyrid-3-yl)-propyl 1,4-dihydro-2,6-dimethyl-4-(4-sulphoxyphenyl)-pyridine 3,5-dicarboxylate

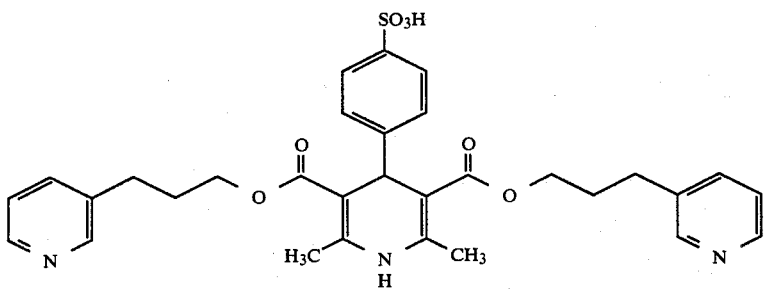

15 g of 3-(pyrid-3-yl)-propyl acetoacetate together with 2.55 ml of 25% strength aqueous ammonia solution and 6.3 g of 4-formylbenzenesulphonic acid in 60 ml of isopropanol are heated under reflux for 24 hours. The reaction mixture is filtered and evaporated down. The residue crystallizes from a mixture of dichloromethane with a small amount of methanol.

Yield: 9.6 g (48% of theory).
Melting point: 130° C. (decomposition).

Example 4

Di-3-(pyrid-3-yl)-propyl 1,4-dihydro-2,6-dimethylpyridine-3,5-dicarboxylate

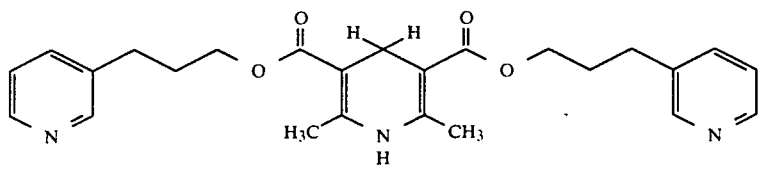

5 g of 3-(pyrid-3-yl)-propyl acetoacetate together with 0.85 ml of 25% strength aqueous ammonia solution and 0.89 ml of 35% strength aqueous formaldehyde solution in 20 ml of isopropanol are heated under reflux for 4 hours. The mixture is then evaporated down in vacuo. The residue crystallizes from ether.

Yield: 1.4 g (28% of theory).
Melting point: 130° C.

Example 5

4-Methyl 3,5-di-3-(pyrid-3-yl)-propyl 1,4-dihydro-2,6-dimethyl-pyridine-3,4,5-tricarboxylate

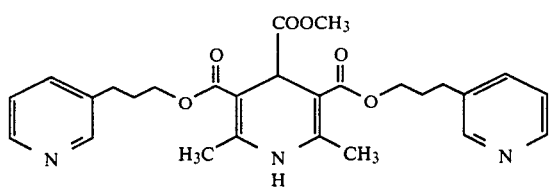

25.1 g of 3-(pyrid-3-yl)-propyl acetoacetate together with 5 g of methyl glyoxalate and 4.24 ml of 25% strength aqueous ammonia solution in 100 ml of isopropanol are heated under reflux for 1.5 hours. The reaction solution is evaporated down, the residue is taken up in ethyl acetate, and the solution is washed 3 times with 2 molar sodium hydroxide solution. The organic phase is dried with sodium sulphate and evaporated down. The residue crystallizes from ether.

Yield: 8 g (28% of theory).
Melting point: 118° to 122° C.

Example 6

Di-3-(pyrid-3-yl)-propyl 4-(4-carboxyphenyl)-1,4-dihydro-2,6-dimethylpyridine-3,5-dicarboxylate

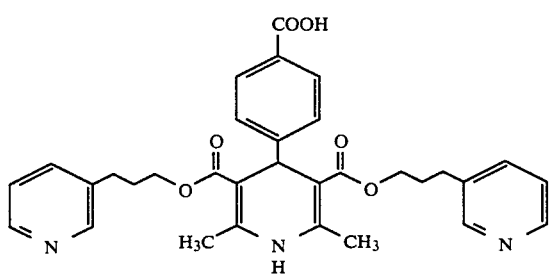

3-(pyrid-3-yl)-propyl acetoacetate together with 7.5 g of 4-formylbenzoic acid and 4 ml of 25% strength aqueous ammonia solution in 80 ml of isopropanol are heated under reflux for 2 hours. The reaction solution is evaporated down, and the residue crystallizes from a mixture of isopropanol with ethyl acetate.

Yield: 11.7 g (42% of theory).
Melting point: 165° to 168° C.

Example 7

Di-(pyrid-3-yl)-methyl 4-(4-carboxyphenyl)-1,4-dihydro-2,6-dimethyl-pyridine-3,5-dicarboxylate

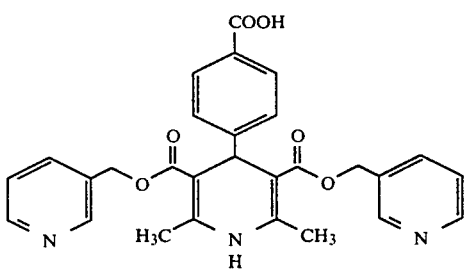

8.6 g of pyrid-3-ylmethyl acetoacetate together with 3.75 g of 4-formylbenzoic acid and 2 ml of 25% strength aqueous ammonia solution in 40 ml of isopropanol are heated under reflux for 2 hours. The reaction solution is thoroughly evaporated down, and the residue crystallizes from ethyl acetate.

Yield: 8 g (64% of theory).
Melting point: 205° to 207° C.

Example 8

Di-3-(pyrid-3-yl)-propyl 1,4-dihydro-2,6-dimethyl-4-[4-[N-(4-(2,3,4,5-tetrahydro-3-oxo-pyridazin-6-yl)phenyl)]carbamoylphenyl]-pyridine-3,5-dicarboxylate

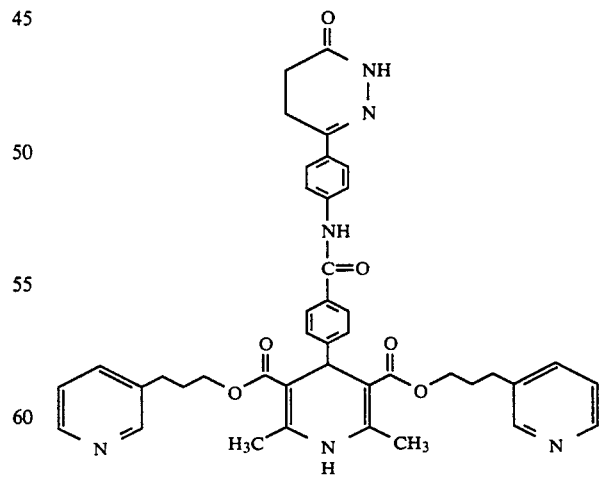

2.2 g of di-3-(pyrid-3-yl)-propyl 4-(4-carboxyphenyl)-1,4-dihydro-2,6-dimethyl-pyridine-3,5-dicarboxylate are dissolved in 20 ml of dry dimethylformamide, and 1 ml of triethylamine is added. After this solution has been cooled to −60° C., 0.31 ml of methanesulphonyl chloride is added dropwise at this temperature, and the reaction mixture is stirred at −60° C. for 15 minutes. Thereafter, 0.8 g of 6-(4-aminophenyl)-2,3,4,5-tetrahydro-3-oxo-pyridazine, dissolved in 20 ml of dry dimethylformamide, is added dropwise at −60° C. The reaction mixture is allowed to warm up to room temperature slowly and is stirred for a further 3 hours at room temperature. The reaction mixture is diluted with water, and extracted 3 times with ethyl acetate. The combined ethyl acetate phases are washed once with 1 molar sodium hydroxide solution, dried with sodium sulphate and evaporated down. In this manner, 1.4 g of solid foam are obtained.

Yield: 1.4 g (48% of theory).
Melting point: 61° to 66° C.

Example 9

Di-3-(pyrid-3-yl)-propyl 1,4-dihydro-2,6-dimethyl-4-[4-N-(pyrid-3-yl)-carbamoylphenyl]pyridine-3,5-dicarboxylate

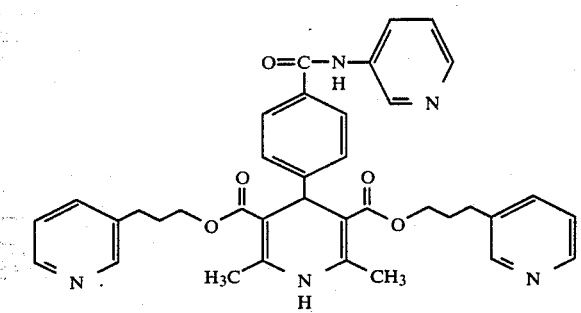

2 g of di-3-(pyrid-3-yl)-propyl 4-(carboxyphenyl)-1,4-dihydro-2,6-dimethyl-pyridine-3,5-dicarboxylate are dissolved in 15 ml of dimethylformamide, and 0.74 g of dicyclohexylcarbodiimide and 0.46 g of N-hydroxysuccinimide are added. After the mixture has been stirred for 1 hour at 0° C., 0.34 g of 3-aminopyridine are added and the reaction mixture is stirred for 3 days at room temperature. Thereafter, stirring is continued for a further 3 hours at 40° C., and the reaction mixture is filtered and diluted with ethyl acetate. The ethyl acetate solution is washed 3 times with water, and the organic phase is dried with magnesium sulphate and evaporated down. The residue is chromatographed over silica gel using a mixture of dichloromethane and methanol in a ratio of 95:5 as the eluent. In this manner, a fraction which gives 1.24 g of solid product after being evaporated down was obtained.

Yield: 1.24 g (54% of theory).

Example 10

Di-3-(pyrid-3-yl)-propyl 1,4-dihydro-2,6-dimethyl-4-[4-N-(pyrid-3-ylmethyl)-carbamoylphenyl]-pyridine-3,5-dicarboxylate

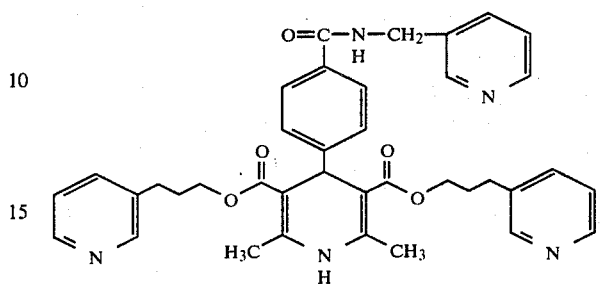

2 g of di-3-(pyrid-3-yl)-propyl 4-(4-carboxyphenyl)-1,4-dihydro-2,6-dimethylpyridine-3,5-dicarboxylate together with 0.74 g of dicyclohexylcarbodiimide in 15 ml of dimethylformamide are initially introduced and cooled to 5° C. After the mixture has been stirred for 15 minutes at this temperature, 0.39 g of 3-picolylamine is added, and the reaction mixture is stirred for 1 hour at 5° C. Thereafter, the reaction mixture is allowed to stand at room temperature for 3 days and is filtered off from the precipitated urea under suction, and the filtrate is evaporated down. The residue is chromatographed over silica gel using a mixture of dichloromethane and methanol in a ratio of 95:5. In this way, a fraction which gives 0.8 g of solid product after being evaporated down is obtained.

Yield: 0.8 g (34% of theory).
Melting point: 57° to 63° C.

Example 11

Di-3-(pyrid-3-yl)-propyl 4-[4-N-(2-furylmethyl)-carbamoylphenyl]-1,4-dihydro-2,6-dimethyl-pyridine-3,5-dicarboxylate

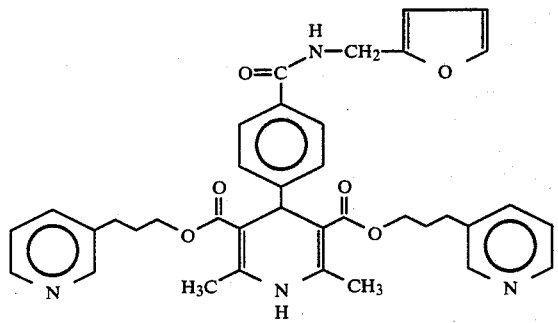

2 g of di-3-(pyrid-3-yl)-propyl 4-(4-carboxyphenyl)-1,4-dihydro-2,6-dimethylpyridine-3,5-dicarboxylate are dissolved in 15 ml of dimethylformamide, and 0.74 g of dicyclohexylcarbodiimide and 0.46 g of N-hydroxysuccinimide are added at 0° C. After the mixture has been stirred for 1 hour at 0° to 5° C., 0.35 g of furfurylamine is added, and the reaction mixture is stirred for 3 hours at room temperature. Thereafter, the reaction mixture is filtered, and diluted with ethyl acetate. The ethyl acetate solution is washed 3 times with water, and the organic phase is dried with magnesium sulphate and evaporated down. The residue is chromatographed over silica gel using a mixture of toluene and acetone in a ratio of 1:1 as the eluent. In this manner, a fraction which gives 0.98 g of solid product after being evaporated down is obtained.

Yield: 0.98 g (43% of theory).
Melting point: 51°–58° C.

Example 12

Di-3-(pyrid-3-yl)-propyl 1,4-dihydro-2,6-dimethyl-4-(4-N-phenylcarbamoyl-phenyl)-pyridine-3,5-dicarboxylate

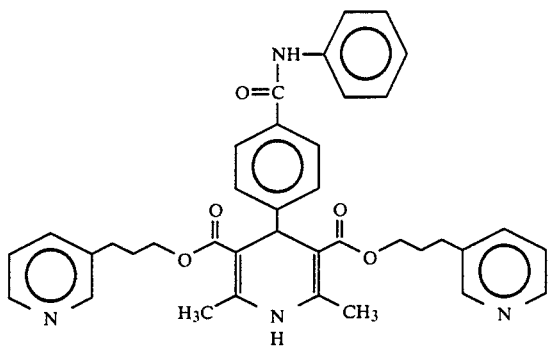

2 g of di-3-(pyrid-3-yl)-propyl 4-(4-carboxyphenyl)-1,4-dihydro-2,6-dimethyl-pyridine-3,5-dicarboxylate are reacted with 0.7 g of dicyclohexylcarbodiimide, 0.46 g of N-hydroxysuccinimide and 0.34 g of aniline in a manner analogous to Example 10. The working up and chromatographic separation are also effected analogously to Example 10.

Yield: 1 g (44% of theory).
Melting point: 49°–55° C.

Example 13

Di-3-(pyrid-3-yl)-propyl 4-(4-N-benzylcarbamoylphenyl)-1,4-dihydro-2,6-dimethyl-pyridine-3,5-dicarboxylate

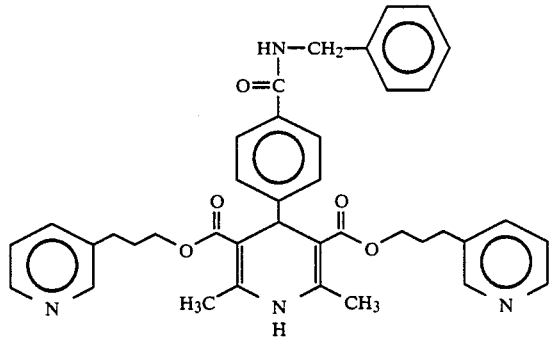

2 g of di-3-(pyrid-3-yl)-propyl 4-(carboxyphenyl)-1,4-dihydro-2,6-dimethyl-pyridine-3,5-dicarboxylate are reacted with 0.74 g of dicyclohexylcarbodiimide, 0.46 g of N-hydroxysuccinimide and 0.39 g of benzylamine in a manner analogous to Example 10. The working up and the chromatographic separation are also effected analogously to Example 10.

Yield: 1 g (43% of theory).
Melting Point: 140°–145° C.

It will be understood that the specification and examples are illustrative but not limitative of the present invention and that other embodiments within the spirit and scope of the invention will suggest themselves to those skilled in the art.

What is claimed is:

1. A 1,4-dihydropyridine of the formula

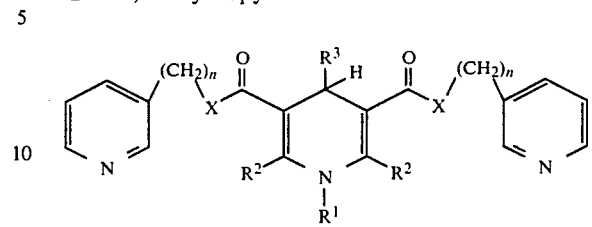

in which
R$^1$ is hydrogen, alkyl having 1 to 5 carbon atoms or alkyl having 1 to 5C atoms and optionally substituted by carboxyl or alkoxycarbonyl having 1 to 4C atoms,
R$^2$ is hydrogen, or alkyl having 1 to 5C atoms,
R$^3$ is hydrogen, alkyl having 1 to 6C atoms, carboxyl, alkoxycarbonyl having 1 to 4C atoms, aryl having 6 to 19C atoms or aryl having 6 to 10C atoms and substituted by hydroxyalkyl, acetoxyalkyl or benzoyloxyalkyl, each having up to 2C atoms in each alkyl group, or by carboxyl, sulphoxyonyl or

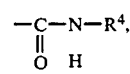

and
R$^4$ is alkyl having 1 to 4C atoms, phenyl, benzyl, pyridyl, pyridylmethyl, furfuryl
X is oxygen, sulphur or NH, and
n is 1 to 6, or a physiologically acceptable salt thereof.

2. A compound or salt according to claim 1, in which
R$^1$ is hydrogen, or alkyl having 1 to 4C atoms,
R$^2$ is alkyl having 1 to 5C atoms,
R$^3$ is hydrogen, alkyl having 1 to 6C atoms, carboxyl, alkoxycarbonyl having 1 to 4C atoms, aryl having 6 to 10C atoms or aryl having 6 to 10C atoms and substituted by hydroxymethyl, acetoxymethyl, carboxyl, sulphoxy or

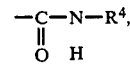

R$^4$ is alkyl having 1 to 4C atoms, phenyl, benzyl, pyridyl, pyridylmethyl, furfuryl.

3. A compound according to claim 1, wherein such compound is di-3-(pyrid-3-yl)-propyl 1,4-dihydro-4-(4-hydroxymethyl-phenyl)-2,6-dimethylpyridine-3,5-dicarboxylate of the formula

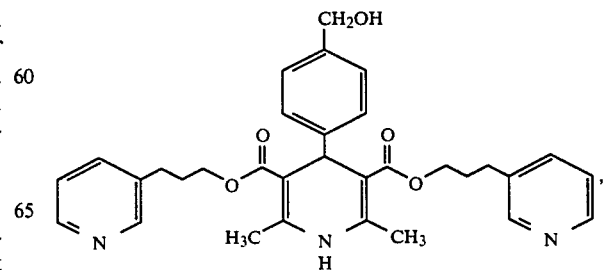

or a physiologically acceptable salt thereof.

4. A compound according to claim 1, wherein such compound is di-3-(pyrid-3-yl)-propyl 1,4-dihydro-2,6-dimethylpyridine-3,5-dicarboxylate of the formula

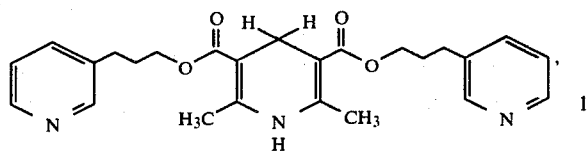

or a physiologically acceptable salt thereof.

5. A compound according to claim 1, wherein such compound is 4-methyl 3,5-di-3-(pyrid-3-yl)-propyl 1,4-dihydro-2,6-dimethylpyridine-3,4,5-tricarboxylate of the formula

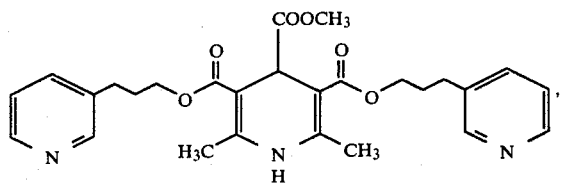

or a physiologically acceptable salt thereof.

6. A compound according to claim 1, wherein such compound is di-3-(pyrid-3-yl)-propyl 1,4-dihydro-2,6-dimethyl-4-[4-N-(pyrid-3-ylmethyl)-carbamoylphenyl]-pyridine-3,5-dicarboxylate of the formula

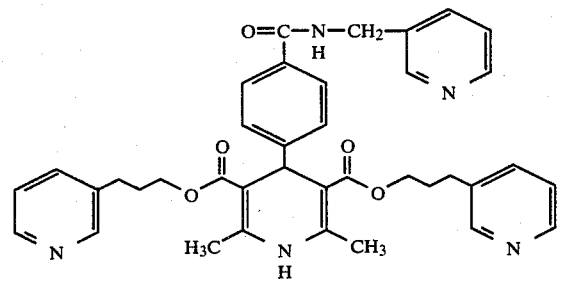

or a physiologically acceptable salt thereof.

7. A compound according to claim 1, wherein such compound is di-3-(pyrid-3-yl)-propyl 4-[4-N-(2-furylmethyl)carbamoylphenyl]-1,4-dihydro-2,6-dimethyl-pyridine-3,5-dicarboxylate of the formula

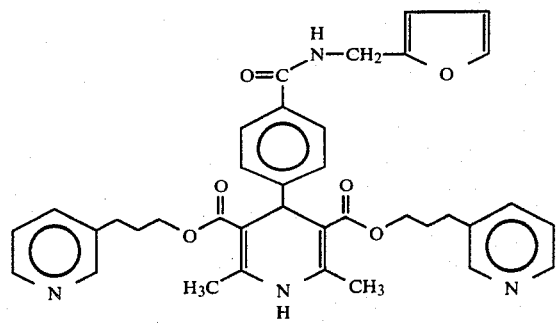

or a physiologically acceptable salt thereof.

8. A composition for combating thromboembolic and ischaemic disorders comprising a diluent and an amount effective therefor of a compound or salt according to claim 1.

9. A method of combating thromboembolic or ischaemic disorders which comprises administering to a patient suffering therefrom an amount effective therefor of a compound or salt according to claim 1.

10. The method according to claim 9, wherein such compound is
di-3-(pyrid-3-yl)-propyl 1,4-dihydro-4-(4-hydroxymethyl-phenyl)-2,6-dimethylpyridine-3,5-dicarboxylate,
di-3-(pyrid-3-yl)-propyl 1,4-dihydro-2,6-dimethylpyridine-3,5-dicarboxylate,
4-methyl 3,5-di-3-(pyrid-3-yl)-propyl 1,4-dihydro-2,6-dimethylpyridine-3,4,5-tricarboxylate,
di-3-(pyrid-3-yl)-propyl 1,4-dihydro-2,6-dimethyl-4-[4-N-(pyrid-3-ylmethyl)-carbamoylphenyl]-pyridine-3,5-dicarboxylate or
di-3-(pyrid-3-yl)-propyl 4-[4-N-(2-furylmethyl)carbamoylphenyl]-1,4-dihydro-2,6-dimethyl-pyridine-3,5-dicarboxylate,
or a physiologically acceptable salt thereof.

* * * * *

UNITED STATES PATENT AND TRADEMARK OFFICE
CERTIFICATE OF CORRECTION

PATENT NO. : 4,686,229

DATED : August 11, 1987

INVENTOR(S) : Ulrich Rosentreter, et al.

It is certified that error appears in the above-identified patent and that said Letters Patent is hereby corrected as shown below:

On the title page

Abstract, line 10 — Delete "acloxyalkyl" and substitute --acyloxyalkyl--

Column 3, line 20 — Middle of structure delete "$(CH_2)_x$" and substitute --$(CH_2)_1$--

Col. 10, line 37 — Top middle of formula delete "$CH_3OH$" and substitute --$CH_2OH$--

Signed and Sealed this

Twelfth Day of April, 1988

Attest:

DONALD J. QUIGG

Attesting Officer

Commissioner of Patents and Trademarks